US010111999B2

(12) United States Patent
Muennich et al.

(10) Patent No.: US 10,111,999 B2
(45) Date of Patent: Oct. 30, 2018

(54) MEDICAL RESERVOIRS WITH VARIABLE-ELEVATION DROP TUBES

(71) Applicant: Terumo Cardiovascular Systems, Inc., Ann Arbor, MI (US)

(72) Inventors: Gregory Peter Muennich, Georgetown, MD (US); Michael Washko, Bear, DE (US); Timothy John Canatella, Jarrettsville, MD (US)

(73) Assignee: Terumo Cardiovascular Systems Corporation, Ann Arbor, MI (US)

( * ) Notice: Subject to any disclaimer, the term of this patent is extended or adjusted under 35 U.S.C. 154(b) by 224 days.

(21) Appl. No.: 15/182,925

(22) Filed: Jun. 15, 2016

(65) Prior Publication Data
US 2017/0361011 A1   Dec. 21, 2017

(51) Int. Cl.
*A61M 37/00* (2006.01)
*A61M 1/36* (2006.01)
*A61M 1/16* (2006.01)

(52) U.S. Cl.
CPC ........ *A61M 1/3666* (2013.01); *A61M 1/1629* (2014.02); *A61M 1/1698* (2013.01); *A61M 1/3627* (2013.01)

(58) Field of Classification Search
CPC .... A61M 1/14; A61M 1/3666; A61M 1/1629; A61M 1/1698; A61M 1/3627
USPC .............................. 604/4.01–6.16; 422/44–48
See application file for complete search history.

(56) References Cited

U.S. PATENT DOCUMENTS

| 4,071,266 | A  |   | 1/1978  | Mountford |
|-----------|----|---|---------|-----------|
| 5,564,465 | A  |   | 10/1996 | Pettesch  |
| 6,050,220 | A  |   | 4/2000  | Kimmel et al. |
| 2007/0239097 | A1 | * | 10/2007 | Nakayama .......... A61M 1/3627 604/6.09 |

* cited by examiner

*Primary Examiner* — Philip R Wiest
(74) *Attorney, Agent, or Firm* — Fish & Richardson P.C.

(57) ABSTRACT

Devices and methods for enhancing the operations of fluid systems are provided. For example, this document provides variable-elevation drop tubes that are well suited for use with medical fluid reservoirs. While the variable-elevation drop tubes provided herein are described in the context of a medical fluid system, such as an extracorporeal blood flow circuit, it should be understood that the devices and methods provided herein are not limited to such contexts.

19 Claims, 4 Drawing Sheets

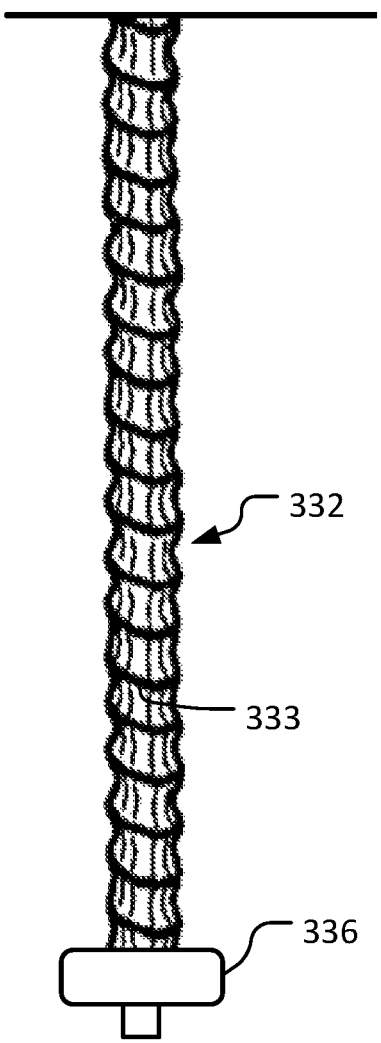
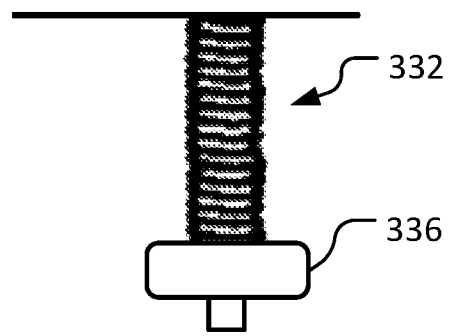
FIG. 5
FIG. 4

MEDICAL RESERVOIRS WITH VARIABLE-ELEVATION DROP TUBES

BACKGROUND

1. Technical Field

This document relates to devices and methods for enhancing the operations of fluid systems. For example, this document relates to variable-elevation drop tubes that are well suited for use with medical fluid reservoirs.

2. Background Information

Fluid systems commonly include components such as tubing, pumps, reservoirs, heat exchangers, sensors, filters, valves, and the like. Such components can be connected together in a network to define a fluid flow path. Some fluid systems are open systems, meaning that the fluid flows through the network once and then exits the network. Other fluid systems are closed systems, meaning that the fluid recirculates within the network of components. Fluids are caused to flow in the fluid system using fluid pressure differentials. In some cases, a pump is used to create a pressure differential that causes the fluid to flow within the fluid system. In some cases, a vacuum source is used to create a pressure differential that causes the fluid to flow within the fluid system. In some cases, gravity is used to create a pressure differential that causes the fluid to flow within the fluid system. In some cases, a combination of such techniques is used to cause fluid flow within the fluid system.

Reservoirs are used as components of fluid systems for various purposes. In some cases, reservoirs are used for accumulation or storage of the fluid. In some cases, the storage of a fluid in a reservoir is used to facilitate a steady outgoing flow of the fluid, despite having an unsteady incoming flow of the fluid. Reservoirs can also be used to facilitate control of the pressure of the fluid within the fluid system. Some reservoirs are completely filled with the fluid, while other reservoirs include an airspace above the level of the fluid in the reservoir.

Drop tubes can be used to introduce a fluid into a reservoir. Such drop tubes can reduce the agitation and turbulence of the fluid as it enters the reservoir, since the outlet of the drop tube is typically below the surface of the fluid in the reservoir. By reducing agitation and turbulence of the fluid, unwanted effects such as air entrainment into the fluid can be controlled.

SUMMARY

This document provides devices and methods for enhancing the operations of fluid systems. For example, this document provides variable-elevation drop tubes that are well suited for use with medical fluid reservoirs.

In one aspect, the disclosure is directed to a medical fluid reservoir that includes a reservoir shell defining an interior space configured for containing a medical fluid; a drop tube disposed within the interior space and defining a drop tube length; and a buoyant member coupled to a portion of the drop tube adjacent the second end. The drop tube length adjusts in response to movement of the buoyant member. The drop tube has a first end that is coupled to the reservoir shell and a second end that has freedom to move within the interior space.

Such a medical fluid reservoir may optionally include one or more of the following features. The medical fluid reservoir may also include a filter material disposed about the drop tube and the buoyant member such that fluid flowing from the drop tube has to pass through the filter materials before exiting the reservoir shell. The medical fluid reservoir may also include a filter frame that provides structural support for the filter material. The buoyant member may be slidably coupled with the filter frame. The drop tube may include a coiled tube. The drop tube may include a corrugated tube. The drop tube may include a telescoping tube. The drop tube may include a bellows. The medical fluid reservoir may also include a blood oxygenation device coupled to the reservoir shell.

In another aspect, the disclosure is directed to a medical fluid reservoir including a reservoir shell defining an interior space configured for containing a medical fluid; a drop tube disposed within the interior space; and a buoyant member coupled to a portion of the drop tube adjacent the second end. A distance between the second end and the fluid outflow port changes in response to movement of the buoyant member. The reservoir shell also defines a fluid outflow port. The drop tube has a first end that is coupled to the reservoir shell and a second end that has freedom to move within the interior space.

Such a medical fluid reservoir may optionally include one or more of the following features. The medical fluid reservoir may also include a filter material disposed about the drop tube and the buoyant member such that fluid flowing from the drop tube has to pass through the filter materials before exiting the reservoir shell through the fluid outflow port. The medical fluid reservoir may also include a filter frame that provides structural support for the filter material. The buoyant member may be slidably coupled with the filter frame. The drop tube may include a coiled tube. The drop tube may include a corrugated tube. The drop tube may include a telescoping tube. The drop tube may include a bellows. The medical fluid reservoir may also include a blood oxygenation device coupled to the reservoir shell. The buoyant member may be configured to maintain a consistent spatial relationship between the second end and a plurality of differing surface levels of a fluid contained in the interior space.

Particular embodiments of the subject matter described in this document can be implemented to realize one or more of the following advantages. First, in some cases the variable-elevation drop tubes provided herein can help to reduce the risk of gaseous emboli in the fluid exiting a medical fluid reservoir. For example, as described further below, by raising the outlet of the drop tube, a greater distance between the outlet of the drop tube and the outlet of the reservoir can be created. Therefore, gaseous emboli entering the reservoir will be given greater opportunity to float to the surface of the fluid where the emboli can be emitted into the gas space above the fluid. Second, in some cases the variable-elevation drop tubes provided herein can help provide better mixing of the fluid in the medical fluid reservoir. Third, in some cases the variable-elevation drop tubes provided herein can help to reduce the risk of stagnation of the fluid in parts of the medical fluid reservoir. In some implementations, blood is the fluid contained in the reservoir and the reduction in stagnation can help prevent thromboemboli (clotted blood) from forming in the reservoir.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 4 is a side view of another variable-elevation drop tube in accordance with some embodiments. The variable-elevation drop tube is shown in a longitudinally elongated configuration.

FIG. 5 is another side view of the variable-elevation drop tube of FIG. 4. The variable-elevation drop tube is shown in a longitudinally contracted configuration.

Like reference numbers represent corresponding parts throughout.

DETAILED DESCRIPTION

This document provides devices and methods for enhancing the operations of fluid systems. For example, this document provides variable-elevation drop tubes that are well suited for use with medical fluid reservoirs. In some cases, a drop tube may also be referred to as a fill tube, inlet tube, and the like.

The devices and methods provided herein are described in the exemplary context of a blood reservoir used for a heart/lung bypass procedure. However, it should be understood that the devices and methods provided herein may be applied in other types of medical fluid systems that include the use of a reservoir, as well as in non-medical applications.

Figure 1:
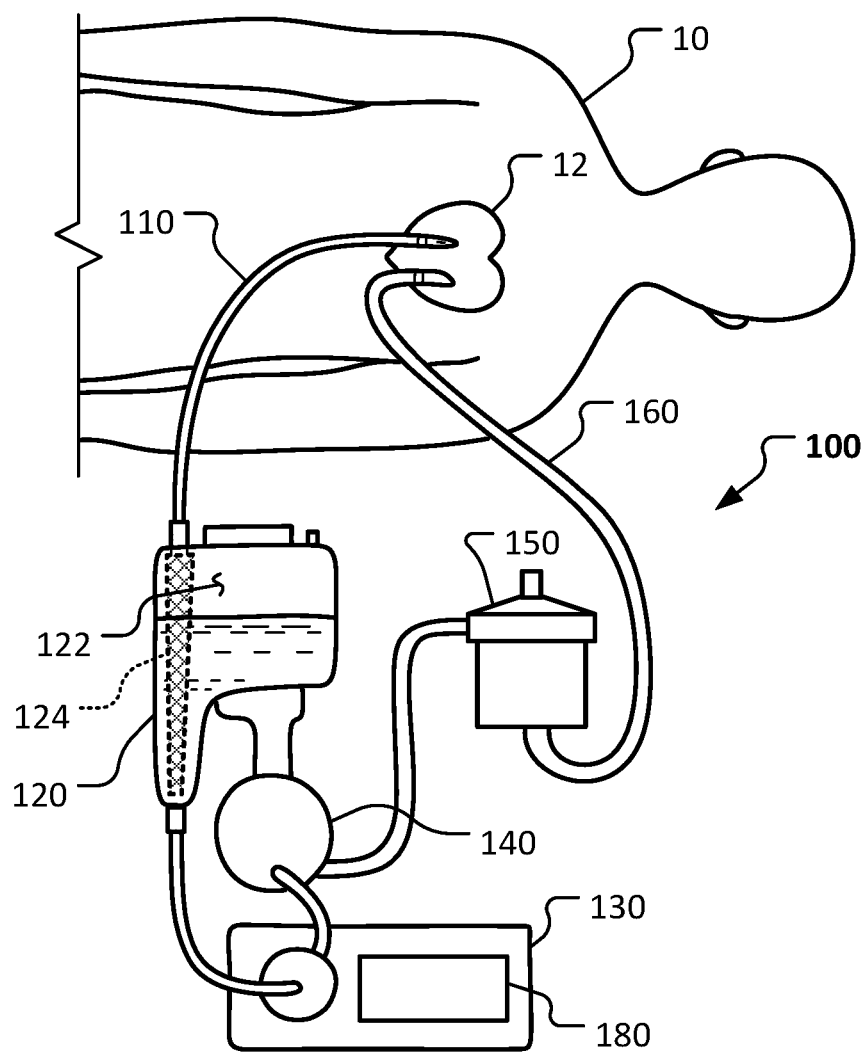
FIG. 1 is a schematic diagram of patient undergoing an example medical procedure using an extracorporeal blood flow circuit that includes a medical fluid reservoir.

Referring to FIG. 1, a patient 10 can receive a medical treatment while using a medical fluid system 100. In this illustrative example, the patient 10 is undergoing a heart bypass procedure using an extracorporeal blood flow circuit 100. The circuit 100 is connected to the patient 10 at the patient's heart 12 (e.g., the right atrium). Blood from the patient 10 is extracted from the patient 10 at the patient's heart 12; the blood is circulated through the circuit 100; and the blood is then returned to the patient's heart 12 (e.g., at the ascending aorta).

The depicted implementation of the extracorporeal blood flow circuit 100 includes, at least, a venous tube 110 (including a cannula), a blood reservoir 120 (e.g., a housing that includes an internal filter 124), a pump 130, an oxygenator/heat exchanger 140, an arterial filter 150 (optional), an arterial tube 160, and a user interface 180. The venous cannula/tube 110 is in physical contact with the heart 12 and in fluid communication with the venous side of the circulatory system of the patient 10. The venous tube 110 is also in fluid communication with an inlet to the reservoir 120.

As described further below, blood from the reservoir inlet is directed to flow through a drop tube that is within the internal filter 124 of the reservoir 120. An outlet from the reservoir 120 is connected by tubing to an inlet of the pump 130. The outlet of the pump 130 is connected to tubing to an inlet of the oxygenator/heat exchanger 140. The outlet of the oxygenator/heat exchanger 140 is connected by tubing to an inlet of the arterial filter 150 (when the arterial filter 150 is included in the circuit 100). An outlet of the arterial filter 150 is connected to the arterial tube 160. The arterial tube 160 is in physical contact with the heart 12 and in fluid communication with the arterial side of the circulatory system of the patient 10. The user interface 180 can include user input and output devices that are used by the clinician operator to properly operate the extracorporeal blood flow circuit 100.

Briefly, the extracorporeal blood flow circuit 100 operates by removing venous blood from the patient 10 via the venous tube 110. Blood from the venous tube 110 is deposited within the internal filter 124 in the reservoir 120. At least some amount of blood is intended to be maintained in the reservoir 120 at all times during the medical procedure. The amount of blood maintained in the reservoir 120 is variable. That is, the level of blood in the reservoir 120 fluctuates over time. The blood passes through the filter 124 located within the reservoir 120. As described further below, the filter 124 can serve to remove potential emboli, including gaseous bubbles, from the blood. That is, in some cases the media of the internal filter 124 has a pore size that prevents through-flow of potential emboli, including gaseous bubbles, that are larger than the pore size.

Blood from the reservoir 120 (after the blood has passed through the filter 124) is drawn from the reservoir 120 by the pump 130. The pump 130 can be operated at various speeds which correspond to various flow rates of blood exiting from the reservoir 120. The pressure generated by the pump 130 propels the blood through the oxygenator/heat exchanger 140. In the oxygenator/heat exchanger 140 the venous blood is enriched with oxygen and adjusted to a desired temperature. The oxygen-rich arterial blood exits the oxygenator/heat exchanger 140, travels through the arterial filter 150 (when the arterial filter 150 is included in the circuit 100), and is injected into the patient's heart 12 by the arterial tube 160.

The flow of blood through the extracorporeal blood flow circuit 100 is intended to be essentially continuous while the medical procedure is taking place. Within that overall context, an accumulation of blood exists in the reservoir 120 during the procedure. The accumulation of a certain amount of blood in the reservoir 120 is advantageous in some circumstances.

The accumulation of blood within the reservoir 120 serves multiple purposes. For example, in one aspect the accumulation of blood in the reservoir 120 provides a buffer amount to help ensure a continuous flow of oxygenated blood to the patient 10, even in the event that blood flow to the reservoir 120 is interrupted. For example, in some cases a clinician operator of the extracorporeal blood flow circuit 100 may endeavor to maintain an amount of blood in the reservoir 120 that allows for about 12 to 15 seconds of runtime (blood flow to the patient 10) in the event that no more blood is added into the reservoir 120. In another example aspect, the reservoir 120 allows the venous blood to deaerate. The deaeration of the venous blood takes place by allowing air bubbles in the blood to escape the blood and flow upward into an airspace 122 within the reservoir 120. For at least that reason, the airspace 122 is generally maintained in the reservoir 120. It can be envisioned from the forgoing description, that when the blood incurs a longer dwell time within the reservoir 120, more opportunity to deaerate the blood is advantageously attained.

From the foregoing description, it should be evident that the amount of blood in the reservoir 120 during a heart bypass procedure fluctuates over time. That is, the level of blood in the reservoir 120 raises and lowers as part of a typical heart bypass procedure.

Figure 2:
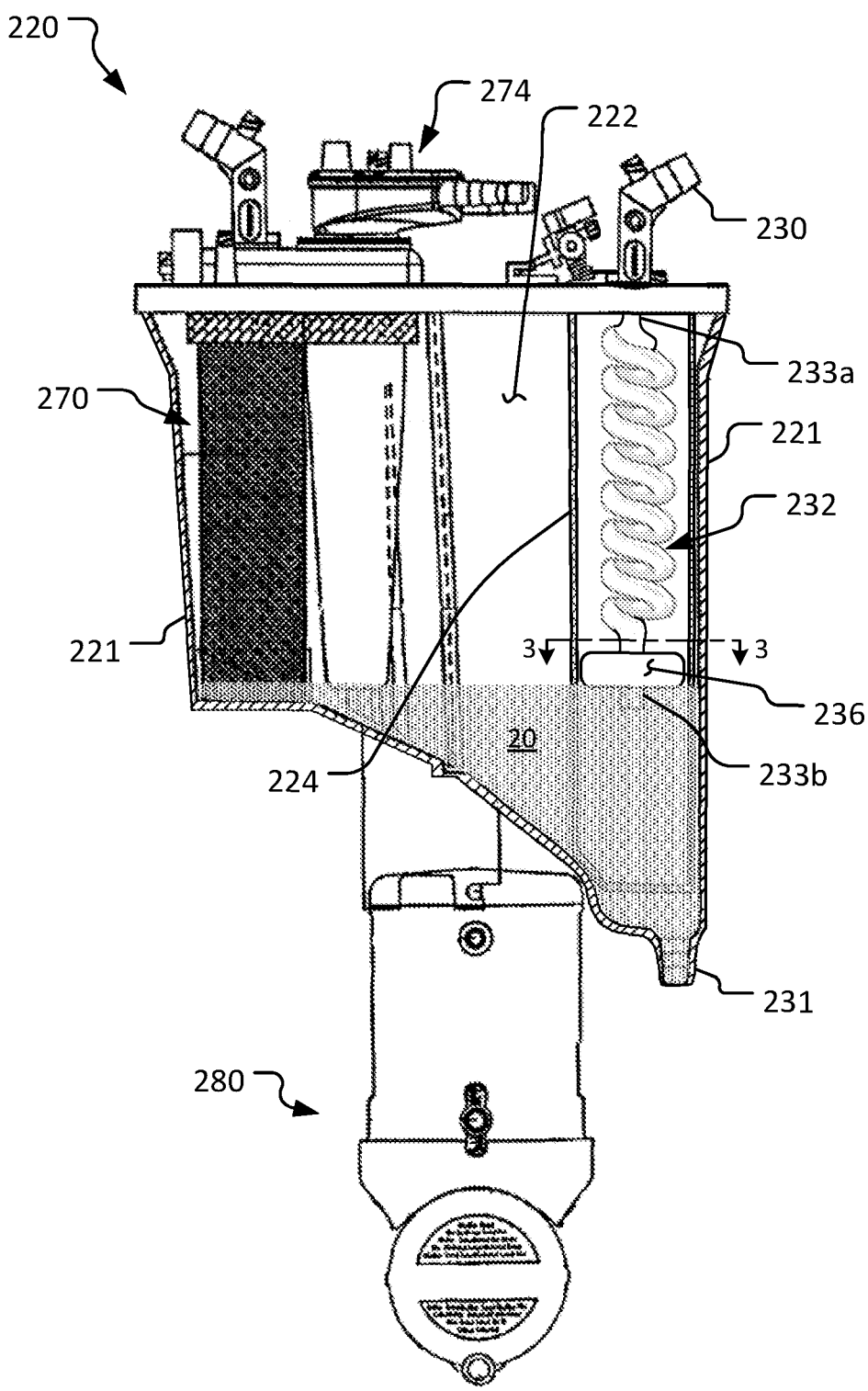
FIG. 2 is a cut away side view of an example medical fluid reservoir including an example variable-elevation drop tube in accordance with some embodiments.

Referring to FIG. 2, an example reservoir 220 that is configured for containing a medical fluid 20 is shown in greater detail. The reservoir 220 can be used in the extracorporeal blood flow circuit 100, for example. In such a case, the medical fluid 20 will be blood (i.e., essentially blood, and potentially containing small amounts of other constituents such as saline, heparin, and the like). It should be understood, however, that the inventive concepts provided herein can also be applied in the context of other types of medical fluid reservoirs, as well as in the context of non-medical reservoirs.

The reservoir 220 includes a reservoir shell 221, an internal filter 224, an inlet fitting 230, an outlet fitting 231, a variable-elevation drop tube 232, and a buoyant member 236. Optionally, in some embodiments additional components are included as part of, or connected to, the reservoir 220. Such optional additional components can include, but are not limited to, a cardiotomy portion with a filter 270, one or more auxiliary ports 274 for sampling and the like, and a blood oxygenator 280. In some cases, a heat exchanger is included in combination with the blood oxygenator 280.

The reservoir shell 221 defines an interior space configured for containing the medical fluid 20. In general, the amount of medical fluid 20 within the interior space is regulated (manually or automatically) such that the reservoir 220 is partially, but not entirely, full. That is, an airspace 222 is typically maintained within the interior space. The reservoir shell 221 can be made of various metallic or polymeric materials such as, but not limited to, polycarbonate. The fluid capacity of the reservoir 220 is scalable to any suitable capacity such as, but not limited to, about 1,000 ml, about 2,000 ml, about 3,000 ml, about 4,000 ml, about 5,000 ml, and any other desirable capacity.

The inlet fitting 230 is coupled to the reservoir shell 221. The inlet fitting 230 is a fluid coupling (e.g., a barb fitting) to which tubing can be attached for supplying fluid into the reservoir 220.

The variable-elevation drop tube 232 is disposed within the interior space defined by the reservoir shell 221. A first end 233a of the drop tube 232 is coupled to the reservoir shell 221 and is in fluid communication with the inlet fitting 230. Therefore, fluids flowing into the reservoir 220 will pass through the inlet fitting 230 and then be transmitted into the lumen defined by the drop tube 232. A second end 233b of the drop tube 232 is a free end. That is, the second end 233b has freedom to move within the interior space defined by the reservoir shell 221.

In the depicted embodiment, the variable-elevation drop tube 232 is a coiled tube made of a flexible material. As such, the drop tube 232 can readily extend and/or retract in length (like a coil spring). As the drop tube 232 extends and/or retracts, the lumen defined by the drop tube 232 remains patent such that fluid can flow therethrough.

The coiled drop tube 232 can be made of any suitable material. Such materials can include, but are not limited to, silicone, polyvinyl chloride (PVC), polyethylene (PE), fluoropolymers (e.g., PTFE, PVDA, PFA, and FEP), and the like, and combinations thereof.

The buoyant member 236 is coupled to the drop tube 232 adjacent to the second end 233b. The buoyant member 236 is lower in density than the medical fluid 20. In result, the buoyant member 236 floats in relation to the medical fluid 20, i.e., the buoyant member 236 floats on (or slightly below) the upper surface of the medical fluid 20. It follows that, as the level of the medical fluid 20 rises or falls, the elevation of the buoyant member 236 rises or falls correspondingly. Moreover, since the buoyant member 236 is coupled to the drop tube 232 adjacent to the second end 233b, the second end 233b of the drop tube 232 rises or falls in correspondence to movements of the buoyant member 236. Said differently, the length of the drop tube 232 adjusts in response to movements of the buoyant member 236, and such movements of the buoyant member 236 can result from changes in the level of the medical fluid 20 within the reservoir 220.

In some embodiments, such as the depicted embodiment, a short end portion of the drop tube extends beyond the buoyant member 236. Accordingly, the end-most tip of the second end 233b will be positioned below the surface of the medical fluid 20 within the interior space of the reservoir 220. Introducing fluid from the second end 233b of the drop tube 232 while it is positioned below the surface of the medical fluid 20 can help reduce fluid turbulence, agitation, as gas entrainment in comparison to having a stream of fluid falling from above to the surface of the medical fluid 20. In some embodiments, the drop tube does not extend beyond the buoyant member 236.

The buoyant member 236 can be made of any suitable material. Such materials can include, but are not limited to, polycarbonate, PVC, PE, silicone, PTFE, PVDA, PFA, and FEP, and the like, and combinations thereof. In some embodiments, the buoyant member 236 is hollow. In some embodiments, the buoyant member 236 has a composite construction that includes a rigid (or semi-rigid) outer shell that covers an inner low-density material (e.g., foam).

The reservoir 220 also includes the internal filter 224. The internal filter 224 is shown in a longitudinal cross-sectional view to provide visibility of the drop tube 232 and the buoyant member 236. The internal filter 224 is disposed about the drop tube 232 and the buoyant member 236 such that fluid flowing into the reservoir 220 via the drop tube 232 must pass through the internal filter 224 in order to exit the reservoir 220.

In some cases, the purpose of the internal filter 224 is to separate unwanted materials from within the medical fluid 20 (e.g., blood), including gaseous bubbles that can become emboli if returned to the patient. As used herein, the term "gaseous emboli" refers to gaseous bubbles whether they reside in a human body or outside the body. In some embodiments, the internal filter 224 is constructed of a mesh material having a particular average opening size (e.g., around 40 microns in some cases). The reservoir 220 also includes the outlet fitting 231. The outlet fitting 231 is coupled to the reservoir shell 221. The outlet fitting 231 is a fluid coupling to which tubing can be attached for conveying fluid that is exiting the reservoir 220.

The drop tube of a conventional reservoir is a fixed drop tube. In other words, typically the drop tube of a conventional reservoir is a rigid tube that remains in a fixed position independent of the level of the fluid contained within the reservoir. Typically, the outlet end of the drop tube of a conventional reservoir is closely located to the outlet fitting 231. The purpose of such an arrangement is to help ensure that fluid entering the reservoir is introduced below the fluid surface (thereby reducing agitation, bubble formation, etc.). In some cases, however, it can be disadvantageous for the outlet end of the drop tube to always be closely located to the outlet fitting 231. For example, in some cases, gaseous emboli exiting the drop tube may tend to flow directly out of the outlet fitting 231 (because of the close proximity between the outlet end of the drop tube and the outlet fitting 231).

In view of the foregoing description, it can be appreciated that a variable-elevation drop tube (such as drop tube 232 in conjunction with buoyant member 236) provides advantages in comparison to a conventional fixed drop tube. For example, while the outlet (second end 233b) of the variable-elevation drop tube 232 tends to always be below the surface of the medical fluid 20, the distance between the drop tube outlet (second end 233b) and the outlet fitting 231 is allowed to increase as the level of the medical fluid 20 rises. As the distance between the drop tube outlet (second end 233b) and the outlet fitting 231 is allowed to increase, the medical fluid's average residence time within the reservoir 220 will increase. Increasing the residence time allows more opportunity for gaseous bubbles within the medical fluid 20 to float upward to the surface of the medical fluid 20 where the bubbles can be released into the airspace 222. In addition, better mixing and reduced stagnation of the medical fluid 20 within the reservoir 220 will tend to result by virtue of the variable-elevation drop tube 232.

Figure 3:
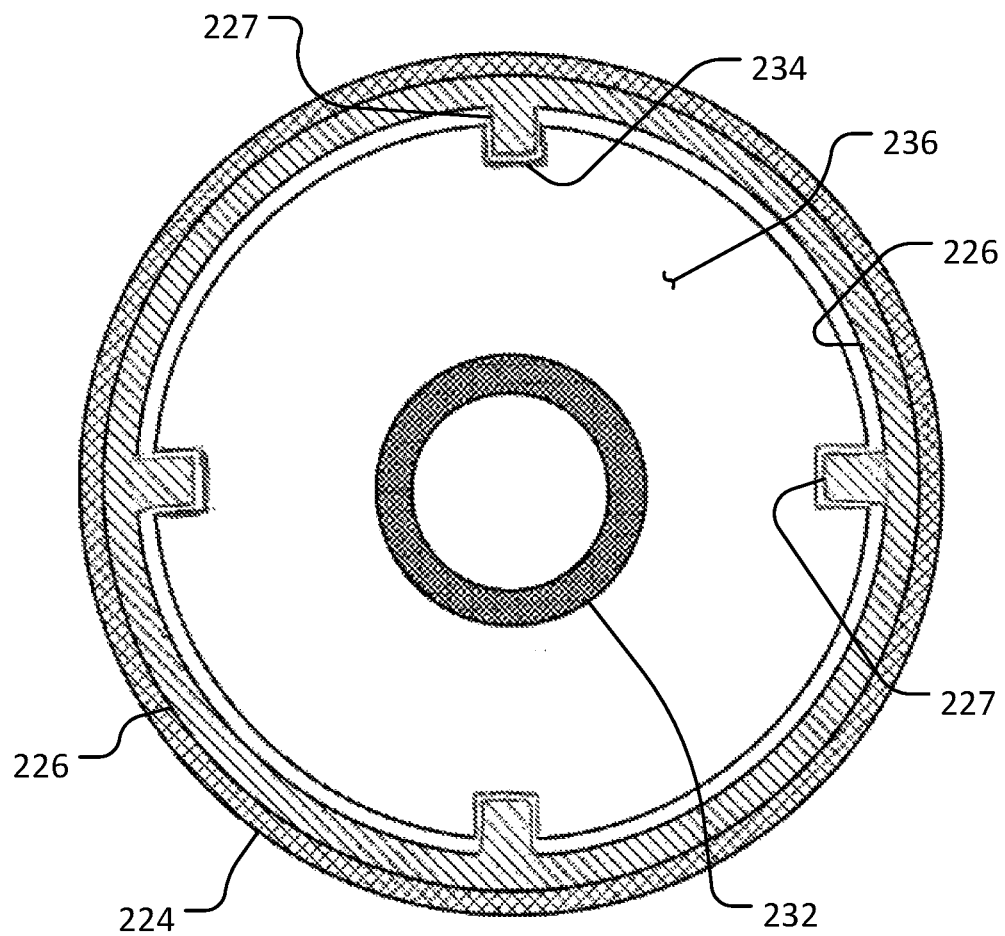
FIG. 3 is a cross-sectional view of the variable-elevation drop tube of FIG. 2.

Referring also to FIG. 3, a transverse cross-sectional view of the internal filter 224 and the drop tube 232 is shown. In some embodiments, a filter frame 226 is included. The internal filter 224 can be disposed on the filter frame 226. The filter frame 226 gives structural support to the otherwise generally flaccid internal filter 224.

In some embodiments, the filter frame 226 is configured such that the buoyant member 236 is slidably coupled with the filter frame 226. For example, in the depicted embodiment the filter frame 226 includes ribs 227 that extend radially inward and that loosely engage with corresponding slots 234 defined by the buoyant member 236. In some embodiments, the filter frame 226 and the buoyant member 236 include no such complementary features (e.g., ribs 227 and slots 234).

While in the depicted embodiment the buoyant member 236 is generally circular in transverse cross-section, other shapes are also envisioned within the scope of this disclosure. For example, in some embodiments the buoyant member 236 is generally ovular, polygonal, or oblong, and the like, in transverse cross-section.

Referring to FIGS. 4 and 5, another example drop tube 332 and buoyant member 336 are illustrated. In this embodiment, the drop tube 332 is a flexible corrugated tube. As described above in reference to drop tube 232, the length of drop tube 332 is adjustable in response to movement of the buoyant member 336 (which is configured to maintain a consistent spatial relationship with a plurality of differing surface levels of a fluid contained in the interior space of a reservoir). As depicted, in some embodiments the drop tube 332 includes a reinforcing element 333 (e.g., a wire).

In some embodiments, the length of drop tube 332 can be biased to its extended configuration (as shown in FIG. 4). In some embodiments, the length of drop tube 332 can be biased to its contracted configuration (as shown in FIG. 5). In some embodiments, the length of drop tube 332 can be biased to a length between its extended configuration and its contracted configuration.

Other types of variable-elevation drop tubes are also envisioned within the scope of this disclosure. For example, in some embodiments the variable-elevation drop tube can be constructed as a telescopic tube. Further, in some embodiments the variable-elevation drop tube can be constructed as a bellows. Still further, in some embodiments the variable-elevation drop tube can be constructed as a rolling bellows. In some embodiments, the variable-elevation drop tube can be constructed as a combination of differing configurations.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A medical fluid reservoir comprising:
   a reservoir shell defining an interior space configured for containing a medical fluid;
   a drop tube disposed within the interior space and configured to introduce the medical fluid into the interior space, the drop tube defining a drop tube length, the drop tube having a first end that is coupled to the reservoir shell and a second end that has freedom to move within the interior space; and
   a buoyant member coupled to a portion of the drop tube adjacent the second end, the drop tube length adjusting in response to movement of the buoyant member.

2. The medical fluid reservoir of claim 1, further comprising a filter material disposed about the drop tube and the buoyant member such that fluid flowing from the drop tube has to pass through the filter materials before exiting the reservoir shell.

3. The medical fluid reservoir of claim 2, further comprising a filter frame that provides structural support for the filter material.

4. The medical fluid reservoir of claim 3, wherein the buoyant member is slidably coupled with the filter frame.

5. The medical fluid reservoir of claim 1, wherein the drop tube comprises a coiled tube.

6. The medical fluid reservoir of claim 1, wherein the drop tube comprises a corrugated tube.

7. The medical fluid reservoir of claim 1, wherein the drop tube comprises a telescoping tube.

8. The medical fluid reservoir of claim 1, wherein the drop tube comprises a bellows.

9. The medical fluid reservoir of claim 1, further comprising a blood oxygenation device coupled to the reservoir shell.

10. A medical fluid reservoir comprising:
a reservoir shell defining an interior space configured for containing a medical fluid, the reservoir shell also defining a fluid outflow port;
a drop tube disposed within the interior space and configured to introduce the medical fluid into the interior space, the drop tube having a first end that is coupled to the reservoir shell and a second end that has freedom to move within the interior space; and
a buoyant member coupled to a portion of the drop tube adjacent the second end, wherein a distance between the second end and the fluid outflow port changes in response to movement of the buoyant member.

11. The medical fluid reservoir of claim 10, further comprising a filter material disposed about the drop tube and the buoyant member such that fluid flowing from the drop tube has to pass through the filter materials before exiting the reservoir shell through the fluid outflow port.

12. The medical fluid reservoir of claim 11, further comprising a filter frame that provides structural support for the filter material.

13. The medical fluid reservoir of claim 12, wherein the buoyant member is slidably coupled with the filter frame.

14. The medical fluid reservoir of claim 10, wherein the drop tube comprises a coiled tube.

15. The medical fluid reservoir of claim 10, wherein the drop tube comprises a corrugated tube.

16. The medical fluid reservoir of claim 10, wherein the drop tube comprises a telescoping tube.

17. The medical fluid reservoir of claim 10, wherein the drop tube comprises a bellows.

18. The medical fluid reservoir of claim 10, further comprising a blood oxygenation device coupled to the reservoir shell.

19. The medical fluid reservoir of claim 10, wherein the buoyant member is configured to maintain a consistent spatial relationship between the second end and a plurality of differing surface levels of a fluid contained in the interior space.

\* \* \* \* \*